United States Patent [19]
Paul et al.

[11] Patent Number: 6,064,478
[45] Date of Patent: May 16, 2000

[54] METHOD OF AND APPARATUS FOR AUTOMATIC DETECTION OF THREE-DIMENSIONAL DEFECTS IN MOVING SURFACES BY MEANS OF COLOR VISION SYSTEMS

[75] Inventors: Detlef Paul; Heribert Geisselmann, both of Stutensee, Germany

[73] Assignees: Fraunhofer-Gesellschaft zur Forderung der angewandten Forschung e.V., Germany; Spectra-Physics VisionTech Oy, Finland

[21] Appl. No.: 08/940,854

[22] Filed: Sep. 29, 1997

[51] Int. Cl.⁷ ................................................. G01N 21/00
[52] U.S. Cl. ................................. 356/237.1; 356/237.2; 356/238.1
[58] Field of Search ................................ 356/237–239, 356/407

[56] References Cited

U.S. PATENT DOCUMENTS

| | | | |
|---|---|---|---|
| 5,245,671 | 9/1993 | Kobayashi | 356/237 |
| 5,298,963 | 3/1994 | Moriya et al. | 356/237 |
| 5,315,384 | 5/1994 | Heffington et al. | 356/237 |

FOREIGN PATENT DOCUMENTS

| | | | |
|---|---|---|---|
| 0 661 108 A2 | 11/1994 | European Pat. Off. | B07C 5/342 |
| 28 43 257 | 4/1979 | Germany | G01B 11/02 |
| 4120749 A1 | 1/1982 | Germany | B01D 3/00 |
| 3150954 A1 | 7/1983 | Germany | G01B 11/00 |
| 4313219 A1 | 11/1994 | Germany | G01N 21/47 |
| 4345106 C2 | 11/1995 | Germany | B07C 5/342 |

*Primary Examiner*—Robert H. Kim
*Assistant Examiner*—Amanda Merlino
*Attorney, Agent, or Firm*—Dougherty & Associates

[57] ABSTRACT

In a method of and an apparatus for detecting three-dimensional defects in the automatic inspection of moving surfaces by means of a color vision system the surface of a moving test specimen which is to be inspected is illuminated with light of different colors simultaneously from at least two different directions, such that edges of three-dimensional defects on the surface appear with a different coloring, and on the basis of the altered coloring, at least two channels of the color image are evaluated to detect three-dimensional defects and to differentiate same from planar defects.

6 Claims, 4 Drawing Sheets

METHOD OF AND APPARATUS FOR AUTOMATIC DETECTION OF THREE-DIMENSIONAL DEFECTS IN MOVING SURFACES BY MEANS OF COLOR VISION SYSTEMS

BACKGROUND OF THE INVENTION

1. Field of the Invention

The invention relates to a method for automatic detection of three-dimensional defects in moving surfaces by means of color vision systems and to an apparatus for performing the method. In particular the invention relates to automatic, real-time inspection of surfaces with respect to defects of different kind and degree, more particular to automatic inspection of moving webs or conveyed piece goods, in which three-dimensional defects, such as indentations, steps, material break-outs, waviness, or dimples, are to be detected, and simultaneously therewith also planar defects defined by color features, texture features and/or geometric features.

2. Description of Prior Art

There is a plurality of vision systems in use for automatic inspection of moving surfaces, e.g. for automatic inspection of paper webs, foils and films, fabrics, steel strips or wood. Most of the systems apply CCD line cameras (gray scale or color) as the sensor for image acquisition, laser scanners being used less frequently. These systems are capturing images, representing e.g. the reflection properties of the surface to be inspected, but containing no direct information on the three-dimensional properties thereof. However, it is generally necessary to detect especially such defects that are characterized by three-dimensional features, such as e.g. indentations, scratches, material break-outs or rough spots. In commonly used systems special techniques for illumination are applied in order to enhance the visibility of three dimensional defects, such that these defects can be detected automatically. However, surfaces in general do not have only three-dimensional defects, but also planar defects, such as stains or discolorations. The images obtained by standard systems do not contain information for distinguishing between planar defects and three-dimensional defects. Therefore in any case a distinction is possible only by means of previous knowledge with respect e.g. to the position or the appearance of different kinds of defects. This procedure fails when the previous knowledge of man cannot be exploited technically or when planar defects may have the same appearance in the image as three-dimensional defects. In such cases, it will be necessary to have information in the image that is in direct relation with the three-dimensional properties of the surface.

For acquisition of three-dimensional information, there is a multiplicity of methods available. These methods can be grouped in two classes: methods giving depth information directly due to their measuring principle (e.g. light section techniques or laser travel-time measurement) and methods exploiting the fact that the reflectance properties of a surface element are dependent upon the orientation and smoothness of the same. The latter methods are referred to as stray light methods. These include a measurement method that is utilized in conjunction with laser scanners. In this method, the surface is scanned with a laser beam, and the reflected light is observed simultaneously from various directions. By comparison of the signals measured in the various channels of observation, it is then possible e.g. to conclude whether the surface element observed is planar or inclined, i.e. whether it is part of a flawless region of a planar, smooth surface or part of the edge of a three-dimensional defect.

Disadvantages of the presently known methods of detecting three-dimensional information in automatic inspection of surfaces are as follows:

Methods for the direct measurement of depth information can be used in surface inspection in exceptional cases only: for most of the applications they are too slow and/or have a too low spatial resolution and/or height resolution.

Laser scanners having a plurality of receiving channels are too expensive for most applications.

For inspection of piece goods, there are modifications of the stray light method in which several images are taken of the test specimen, where the object is being illuminated from different directions for subsequent images.

From the obtained image series it is possible to derive knowledge on the reflectance behavior and the spatial orientation of the surface elements. A prerequisite for employing this method is that the test specimen is at rest. This prerequisite is not fulfilled in applications for automatic inspection of webs, steel or other moving surfaces.

SUMMARY OF THE INVENTION

It is the object of the invention to obtain information on the three-dimensional properties of the inspected surface and, in addition thereto, also information on the gray scale distribution and the color of the surfaces. Three-dimensional defects such as material break-outs, indentations, steps, dimples or projecting parts shall be identifiable clearly as three-dimensional defects and distinguishable from planar defects.

According to a first aspect of the invention, this object is achieved by a method of detecting three-dimensional defects in the automatic inspection of moving surfaces by means of a color vision system, in which the surface of a moving test specimen is illuminated with light of different colors simultaneously from at least two different directions, such that edges of three-dimensional defects on the surface appear with a different coloring, and thus the three dimensional defects can be detected by comparing at least two of the three channels of the color image and it is possible to differentiate same from planar defects.

According to a further aspect of the present invention, this object is achieved by an apparatus for detecting three-dimensional defects in an automatic inspection of moving surfaces by means of a color vision system, which has two light sources of different color arranged transversely to the direction of transportation of the surface to be inspected, such that a measurement line on a test specimen observed by the color line scan camera is illuminated by the two light sources obliquely from different directions, namely in the direction of transportation and opposite thereto.

According to a further aspect of the present invention, this object is achieved by an apparatus for detecting three-dimensional defects in an automatic inspection of surfaces by means of a color vision system, which has only one lamp whose light is coupled into two optical waveguide modules via an optical coupling system provided with color filters designed for the specific application, and by this optical waveguide module the observed measurement line is illuminated obliquely with a strong directional component transversely to the direction of transportation.

According to the invention, for realization of the measuring method, a color vision system is employed, e.g. with a standard color line camera as the sensor device. As a characteristic feature of inventive method a specific kind of illumination is added to the vision system, which is involving either no additional expenditure at all or only relatively little additional expenditure. The signal evaluation and recognition of three-dimensional defects can be achieved by means of the color classifier that is present anyway in a color vision system. As compared to the light section method, for example, the information on three-dimensional defects is obtained with the full spatial resolution of the image taken.

However, direct measurement of the surface relief is possible in exceptional cases only.

The surface to be inspected is observed with a color camera, e.g. with a color line scan camera. By means of a color camera, three measurement values are obtained in registered manner from each point of the surface to be inspected, in general for the color channels "red", "green" and "blue". When the surface is illuminated with white light, an image is obtained in which the surface is represented in natural colors. To recognize three-dimensional defects on the surface, the test specimen, according to the invention, is illuminated from at least two light sources radiating light of different colors from different directions onto the surface. With this kind of illumination, three-dimensional defects on the surface cause shifting of the balance between the color channels when the picture is taken. There are two different effects responsible therefor: shadow-casting and the dependence of the reflectance lobe on the inclination of the surface.

BRIEF DESCRIPTION OF THE DRAWINGS

Preferred embodiments of the present invention are described hereinafter with reference to the appended drawings.

DESCRIPTION OF PREFERRED EMBODIMENTS OF THE INVENTION

Figure 1:
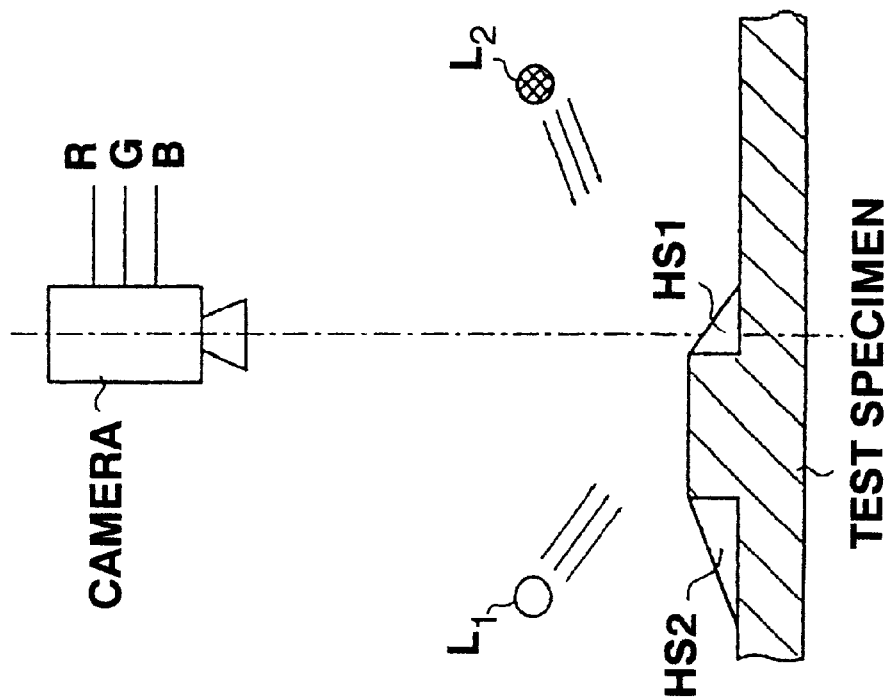
FIGS. 1 and 2 illustrate an embodiment for a surface inspection system by means of a color line scan camera and two lamps.

FIG. 1 shows the conditions for an inclined surface, namely for a surface element at the right-hand edge of an indentation. The surface is illuminated by two lamps L1 and L2 from different directions, assuming e.g. that lamp L1 is red and lamp L2 is blue. The light from lamp L1 is reflected from the element observed on the surface in accordance with the reflectance lobe R1, the light from lamp L2 being reflected in accordance with R2. While R1 and R2 would be substantially symmetrical with each other in case of a planar surface, R1 due to the approximately fulfilled mirror condition has strong components in the direction towards the camera, whereas R2 has only weak ones. As regards the (red) channel of the camera, that is matched to the color of L1, this surface element thus appears especially bright, and for the (blue) channel matched to L2 it appears especially dark. The surface element observed thus will look clearly red in this example.

Figure 2:
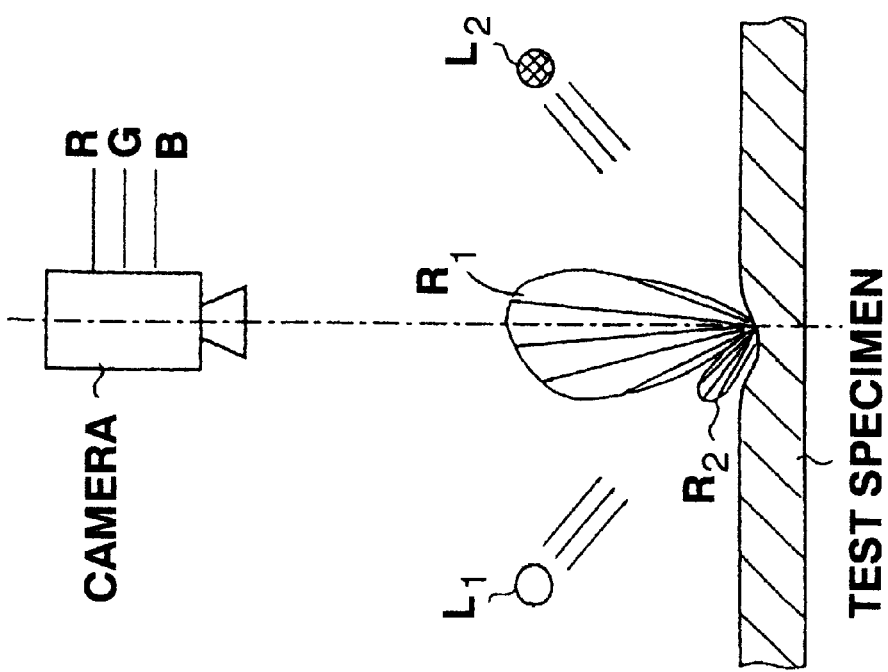

FIG. 2 shows a corresponding effect, caused however by shadow-casting: in case of a step, the balance between the observation channels in the penumbra HS1 and HS2 at the edges of the step is strongly shifted, the image shows distinct color fringes there. The same holds analogously for a groove. Three-dimensional defects thus are recognizable as color changes in the image. It is immediately apparent that the method described can be used advantageously for inspecting monochromatic surfaces, whereas it will fail in inspecting surfaces with an arbitrary richness in color. However, in the field of surface inspection, the richness in color of the surface to be inspected is in general restricted, e.g. with respect to metals, plastics, coated surfaces or wood. Wooden surfaces for example are "colored in restricted manner": they play in different shades of brown, and there are natural color defects such as blueness or red stripes; however, there are e.g. no shades of green. The method may well be used with such "restricted colored" surfaces. It will be possible by means of a correspondingly trained color classifier to decide for each image point whether it belongs to the flawless surface, to a planar defect or a three-dimensional defect.

FIGS. 1 and 2 illustrate an embodiment for a surface inspection by means of a color line scan camera and two lamps, depicted here as fluorescent tubes L1 and L2 with different colors (e.g. "blue" and "red"). The direction of transportation is directed towards the left, the line scan camera and the fluorescent tubes are oriented transversely to the direction of transportation.

Due to the geometric arrangement of lamps and camera, this measurement construction is well suited for detecting defects oriented transversely to the direction of transportation, steps of scratches oriented parallel to the direction of transportation are not detected.

Figure 3:
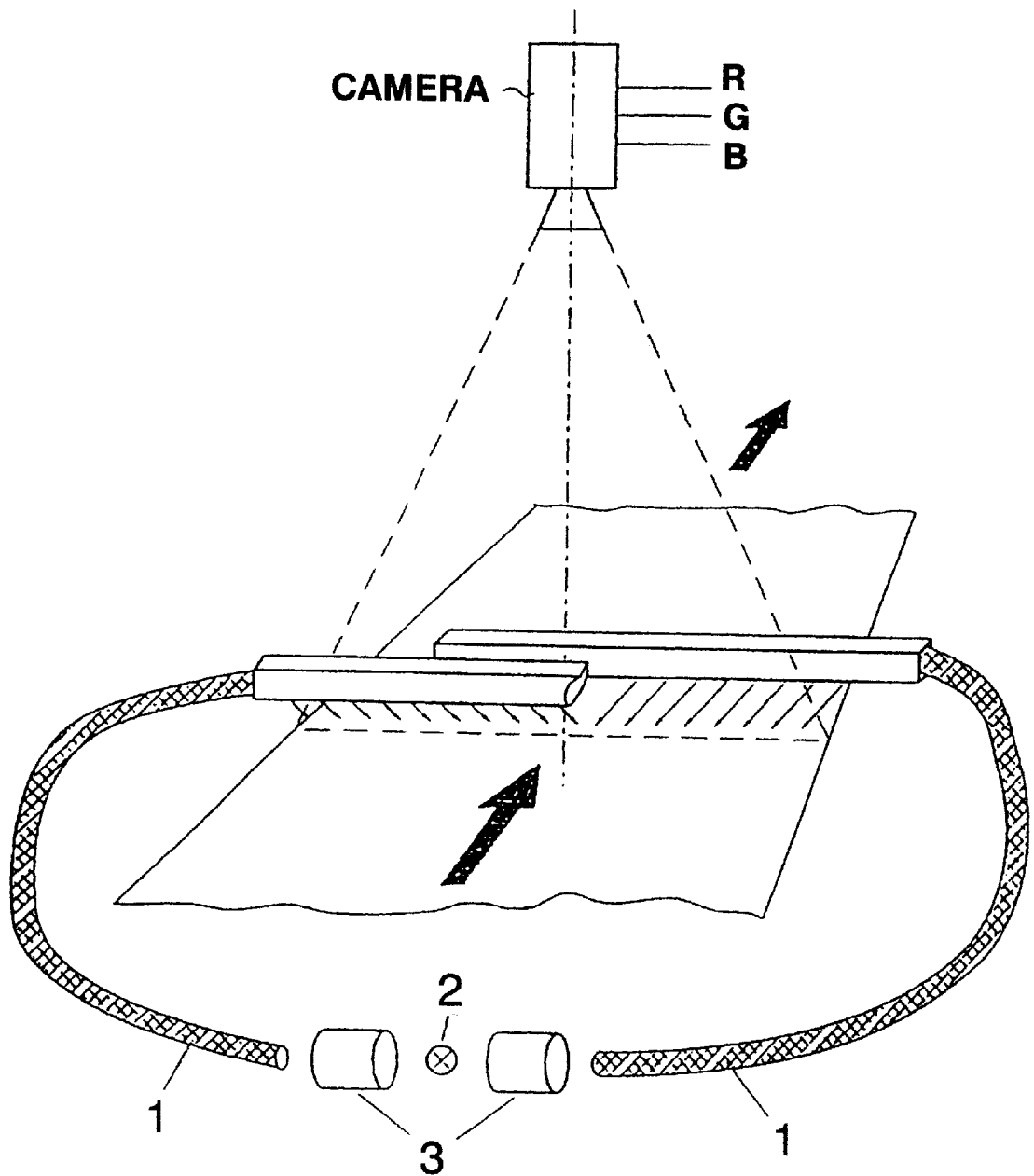
FIG. 3 illustrates an embodiment wherein the direction of illumination is basically perpendicular to the direction of motion instead of parallel.

In the embodiment according to FIG. 3, the direction of illumination is rotated: it now has a strong component transversely to the direction of transportation. This results in particularly good visibility for defects oriented in the direction of transportation.

Figure 4:
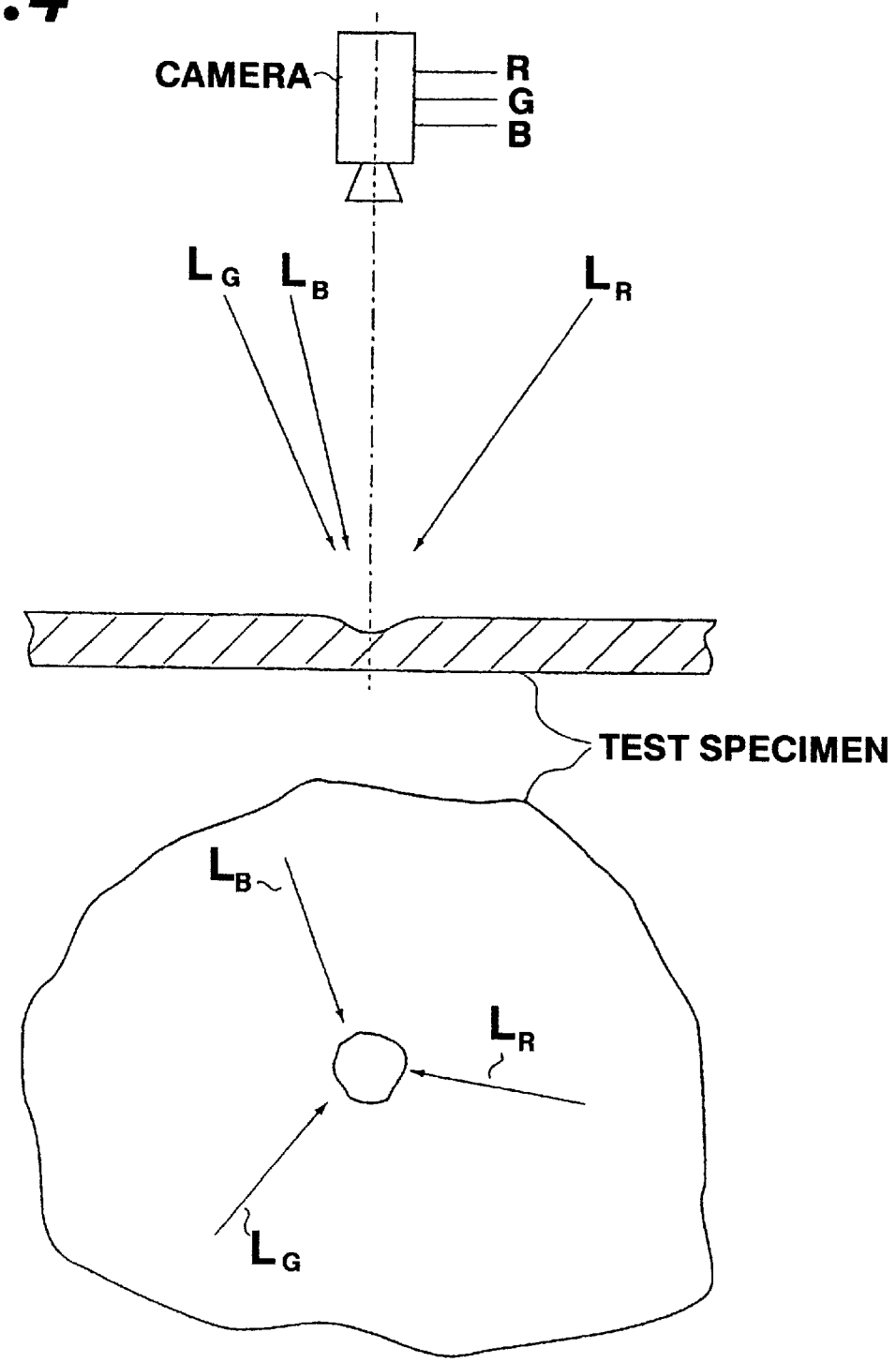
FIG. 4 shows a generalized form of the embodiments shown in FIGS. 1, 2, and 3.
Figure 5:
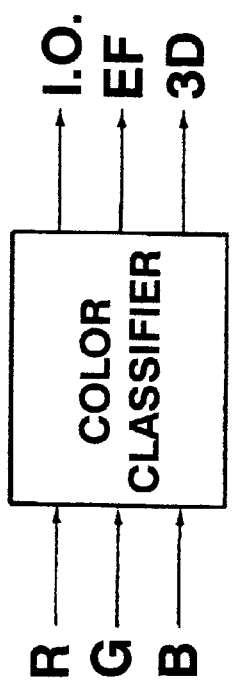
FIG. 5 shows a diagram of a color classifier.

In the embodiment shown, the illumination is realized by an optical waveguide system 1 having a central light source 2. The light is coupled into the optical waveguides via an optical coupling system 3. The optical coupling system 3 contains filters by means of which color and intensity of the two branches of the optical waveguide system 1 can be determined separately from each other. The light leaves the two branches of the optical waveguide system in oblique direction, in each case with a strong component transversely to the direction of transportation of the web. The arrangement with a central light source avoids the effect that intensity fluctuations of the light source are influencing the balance between the color channels. FIG. 4 shows a generalized form of the arrangements according to FIG. 1, FIG. 2 and FIG. 3: in this case, the surface under inspection is illuminated from three directions simultaneously. The strong dependence of the detection probability on the orientation of the defects, existing for the arrangements described hereinbefore, is clearly reduced thereby. For realizing an illumination of this kind, a suitable optical waveguide system may be utilized analogously to FIG. 3. For evaluating the image information recorded, it is possible to use a color classifier according to FIG. 5: after a training phase, the color classifier decides for each pixel in a context-free manner, on the basis of the RGB color value, for "i.o." (flawless surface), "EF" (planar defect) or "3D" (three-dimensional defect).

Any significant deviation from the planar surface is determined to be a three-dimensional defect in this case; an estimate of the surface orientation is omitted.

Figure 6:
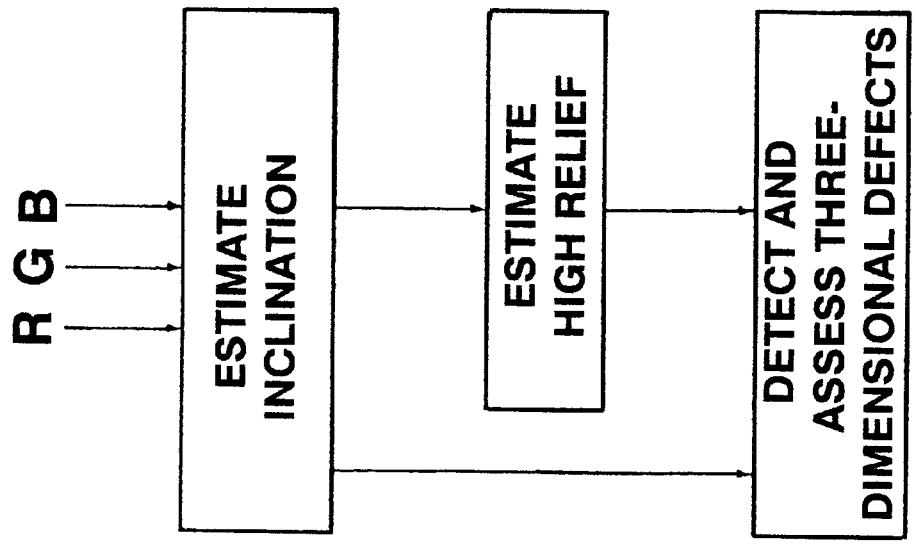
FIG. 6 shows the structure of a more comprehensive evaluation method.

FIG. 6 shows the structure of a more comprehensive evaluation method. In this case, the information on the inclination of the surface elements, which is contained in the picture taken under certain conditions, is used for obtaining an estimate on the surface profile. It is possible to clearly recognize from the sequence of the penumbrae HS1 and HS2 in FIG. 2, for example, that the present three-dimensional defect must be a bulge—in case of a recess, the sequence of the penumbrae would be reversed. In addition thereto, the height of the step concerned can be concluded from the width of the penumbrae HS1 and HS2 in the image. When the diffuse reflectance properties of the surface are known, it is in principle possible to conclude the inclination of the surface elements from the relationship of the measured intensities in the individual channels, and when the inclination is known, the profile of the surface can be obtained by integration over the inclinations.

The measurement method outlined, in practical applications, can deliver only estimates for the inclination of surface elements because the reflectance properties of the surface to be inspected are not known in general. The method shown in FIG. 6 for determining the surface profile is applicable only if reflectance behavior of the surface is known and it must also make use of context information, e.g. in the scope of a relaxation method.

What is claimed is:

1. A method of detecting three-dimensional defects in a continuous web by an automatic inspection of the moving web by means of a color vision system, comprising the steps of:

illuminating a surface of the moving web with light of different colors simultaneously from at least two different directions, such that edges of three-dimensional defects on said surface appear with an altered coloring, and on the basis of the altered coloring, evaluating at least two color channels of a color image to detect three-dimensional defects and to differentiate the three-dimensional defects from planar defects.

2. The method of claim 1, wherein the differentiation between a flawless surface, planar defects and three-dimensional defects is made by a color classifier.

3. The method of claim 1, wherein the type of three-dimensional defects and the degree thereof is judged by evaluating the type, intensity and geometrical arrangement of discolorations of image portions indicating three-dimensional defects, starting with an estimate of the inclination of each surface element.

4. The method of claim 1, wherein two lamps of different color are arranged transversely to a direction of transportation of said web such that a measurement line observed by a color line scan camera is illuminated by said two lamps obliquely from different directions, namely in said direction of transportation and opposite thereto.

5. The method of claim 1, wherein said surface to be inspected is illuminated from three directions, such that said edges of defects with arbitrary orientation become visible in each case by discolorations.

6. An apparatus for detecting three-dimensional defects in a continuous web by an automatic inspection of the moving web by means of a color vision system, which evaluates at least two color channels of a color image to detect three-dimensional defects and to differentiate the three-dimensional defects from planar defects comprising: two light sources of different color arranged transversely to a direction of transportation of a surface of the web to be inspected, such that a measurement line on the web observed by said color vision system is illuminated by said two light sources obliquely from different directions, namely in said direction of transportation and opposite thereto.

* * * * *